US012656333B2

(12) United States Patent
Horev et al.

(10) Patent No.: US 12,656,333 B2
(45) Date of Patent: Jun. 16, 2026

(54) CLINICAL DECISION SUPPORT SYSTEM

(71) Applicant: Instrumentation Laboratory Company, Bedford, MA (US)

(72) Inventors: Benjamin Horev, Littleton, MA (US); Ethan Schonbrun, Auburndale, MA (US); Gert Blankenstein, Munich (DE); Luisa Andruzzi, West Boylston, MA (US); Anne Winkler, Burlington, MA (US); Jacqueline Scott, Pittsburgh, PA (US)

(73) Assignee: Instrumentation Laboratory Company, Bedford, MA (US)

( * ) Notice: Subject to any disclaimer, the term of this patent is extended or adjusted under 35 U.S.C. 154(b) by 680 days.

(21) Appl. No.: 18/086,873

(22) Filed: Dec. 22, 2022

(65) Prior Publication Data
US 2023/0314405 A1     Oct. 5, 2023

Related U.S. Application Data

(60) Provisional application No. 63/325,304, filed on Mar. 30, 2022.

(51) Int. Cl.
*G01N 33/49* (2006.01)
*C12Q 1/56* (2006.01)
(Continued)

(52) U.S. Cl.
CPC .......... *G01N 33/4905* (2013.01); *C12Q 1/56* (2013.01); *G01N 33/86* (2013.01); *G16H 50/20* (2018.01); *G01N 2800/226* (2013.01)

(58) Field of Classification Search
None
See application file for complete search history.

(56) References Cited

U.S. PATENT DOCUMENTS 6,165,795 A     12/2000  Mize et al.
6,524,861 B1 *   2/2003  Anderson .............. G01N 33/86
                                                                422/65
(Continued)

FOREIGN PATENT DOCUMENTS

AU        2009308841 B2     7/2014
CA           2911873 A1    12/2014
(Continued)

OTHER PUBLICATIONS

European Search Report in EP Application No. 23165549.9 dated Dec. 18, 2023, 6 pages.
(Continued)

*Primary Examiner* — Matthew D Krcha
(74) *Attorney, Agent, or Firm* — ARENTFOX SCHIFF LLP

(57)     ABSTRACT

An example method includes: analyzing a clot curve for a test sample that is based on an assay performed on the test sample in order to obtain two or more parameters associated with the clot curve; analyzing the two or more parameters to determine at least one of (i) whether a fibrinogen concentration in the test sample is below a threshold, or (ii) whether there is a therapeutic or pharmaceutical anticoagulant present in the test sample; and outputting, to a user interface, information based on the determination.

19 Claims, 11 Drawing Sheets

(51) Int. Cl.
    *G01N 33/86*    (2006.01)
    *G16H 50/20*    (2018.01)

(56) References Cited

U.S. PATENT DOCUMENTS

| | | | | |
|---|---|---|---|---|
| 2012/0065514 A1* | 3/2012 | Naghavi | ................ | G01K 13/20 |
| | | | | 600/481 |
| 2014/0038205 A1* | 2/2014 | Raynard | ................... | A61P 7/04 |
| | | | | 435/7.8 |
| 2018/0306820 A1 | 10/2018 | Suzuki et al. | | |
| 2019/0101526 A1 | 4/2019 | Brun et al. | | |
| 2021/0140895 A1 | 5/2021 | Muldoon | | |
| 2021/0140985 A1 | 5/2021 | Evans et al. | | |
| 2021/0333295 A1* | 10/2021 | Kawabe | ................ | G01N 33/86 |
| 2022/0002779 A1 | 1/2022 | Kerdelo | | |
| 2024/0077504 A1* | 3/2024 | Kawabe | ................ | G01N 33/86 |

FOREIGN PATENT DOCUMENTS

| | | |
|---|---|---|
| EP | 3971576 | 3/2022 |
| EP | 4212880 A1 | 7/2023 |
| JP | 6994528 B2 | 1/2022 |
| WO | 199201065 | 1/1992 |
| WO | 2022054819 A1 | 3/2022 |

OTHER PUBLICATIONS

Doubleday et al., "Clot Signature Curves and the ACL Advance™," Coagulation 12, Instrumentation Laboratory [online] Retrieved from the Internet: URL:http://de.werfen.com/~/media/il%20shared/docs/ hemostasis/literature/100%20%20%20clot%20signature%20curves% 20and%20the%20acl%20advance.pdf [retrieved on Jan. 23, 2020], (2001), 49 pages.

Partial European Search Report in Application No. 23165549.9 dated Jul. 20, 2023, 14 pages.

European Search Report in EP Application No. 23165549.9 dated Jan. 12, 2024, 7 pages.

Examination Report in Australian Application No. 2023201728 dated Dec. 22, 2023, 10 pages.

Song, J., "Advances in Laboratory Assessment of Thrombosis and Hemostasis," Blood Research, vol. 57, No. S1 (Apr. 2022), 8 pages.

Office Action received for Australian Patent Application No. 2023201728, mailed on Dec. 22, 2023, 10 pages.

Office Action received for Australian Patent Application No. 2023201728, mailed on Oct. 1, 2024, 4 pages.

Office Action received for European Patent Application No. 23165549. 9, mailed on Oct. 25, 2024, 6 pages.

Song., "Advances in laboratory assessment of thrombosis and hemostasis", Blood Research, vol. 57, No. S1, Apr. 2022, pp. 93-100.

Wada et al., "Update on the Clot Waveform Analysis", Clinical and Applied Thrombosis/Hemostasis, vol. 26, Aug. 30, 2020, pp. 1-8.

Kanouchi et al., "Diagnostic analysis of lupus anticoagulant using clot waveform analysis in activated partial thromboplastin time prolonged cases: A retrospective analysis", Health Science Reports, vol. 4, No. 2, Mar. 12, 2021, pp. 1-7.

Shimomura et al., "The First-Derivative Curve of the Coagulation Waveform Reveals the Cause of aPTT Prolongation", Clinical and Applied Thrombosis/Hemostasis, vol. 26, 2020, pp. 1-8.

Extended European Search Report received for European Patent Application No. 25221820.1, mailed on Mar. 17, 2026, 10 pages.

\* cited by examiner

INPUT VALUES FOR TWO OR MORE
PARAMETERS TO ONE OR MORE PROCESSES FOR
ANALYZING FIBRINOGEN CONCENTRATION
AND/OR FOR IDENTIFYING THERAPEUTIC OR
PHARMACEUTICAL ANTICOAGULANT — 40a

EXECUTING THE ONE OR MORE PROCESSES
BASED ON THE TWO OR MORE PARAMETERS — 40b

RETURN RESULT BASED ON OUTPUT(S) OF THE
ONE OR MORE PROCESSES — 40c

CLINICAL DECISION SUPPORT SYSTEM

CROSS-REFERENCE TO RELATED APPLICATION

This application claims the benefit of, and priority to, U.S. Provisional Application No. 63/325,304, which was filed on Mar. 30, 2022. The contents of U.S. Provisional Application No. 63/325,304 are incorporated herein by reference.

TECHNICAL FIELD

This specification relates generally to systems and processes for providing clinical decision support relating to fibrinogen concentration and/or therapeutic or pharmaceutical anticoagulants in a test sample.

BACKGROUND

Fibrinogen is a glycoprotein complex, produced in the liver, that circulates in the blood of all vertebrates. During tissue and vascular injury, fibrinogen is converted enzymatically by thrombin to fibrin and then to a fibrin-based blood clot. Fibrin clots function primarily to occlude blood vessels to stop bleeding.

Heparin is a therapeutic or pharmaceutical anticoagulant drug that prevents the formation of blood clots by preventing certain cofactors, namely thrombin and fibrin, from working correctly.

Direct Oral Anticoagulants (DOACs) are therapeutic or pharmaceutical anticoagulant drugs that intervene in the coagulation cascade and that inhibit specific clotting factors, such as Factor Xa and Factor IIa (thrombin).

SUMMARY

An example system includes non-transitory machine-readable memory storing instructions that are executable and one or more processing devices configured to execute the instructions to perform operations that include: analyzing a clot curve for a test sample that is based on an assay performed on the test sample in order to obtain two or more parameters associated with the clot curve, where the two or more parameters include two or more of: clot growth rate, clot formation duration, clot amplitude (which may include sigmoid magnitude range and/or clot curve range), clot baseline, clotting time, clot growth width, clot growth skew, or first, second, or third derivative features of the clot curve that include one or more of clot acceleration duration and/or shape, clot deceleration duration and/or shape, clot peaks width, clot peaks width ratio, clot peaks location, clot peaks number, clot velocity, clot peaks amplitude, clot peaks area under curve (AUC), shapes of clot peaks, peaks onset shape, peak offset shape, peak skewness, peak kurtosis, width at a peak baseline, width at a peak location other than peak baseline, peaks prominence, a parameter based on a maximum acceleration and zero crossing of the clot curve, a parameter based on the maximum acceleration and pre-defined threshold of the clot curve, or a parameter based on maximum and minimum acceleration of the clot curve. The operations also include analyzing the two or more parameters to determine at least one of (i) whether a fibrinogen concentration in the test sample is below a threshold, or (ii) whether there is a therapeutic or pharmaceutical anticoagulant present in the test sample. The example system also includes a user interface. The operations include outputting, on the user interface, information based on the determination. The information based on the determination is obtainable on the user interface. The example system may include one or more of the following features, either alone or in combination.

The information may include a recommendation to perform additional testing for fibrinogen or the therapeutic or pharmaceutical anticoagulant. The information may include a concentration of fibrinogen in the test sample or an identity of the therapeutic or pharmaceutical anticoagulant in the test sample. The two or more parameters may be based on at least one of a first derivative of the clot curve or a second derivative of the clot curve. The therapeutic or pharmaceutical anticoagulant may include at least one of heparin or a direct oral anticoagulant (DOAC), where the DOAC may include at least one of apixaban, dabigatran, or rivaroxaban. Analyzing the two or more parameters to determine whether there is a therapeutic or pharmaceutical anticoagulant present in the test sample may include using the two or more parameters to distinguish the therapeutic or pharmaceutical anticoagulant from a natural or genetically-occurring anti-coagulant, where the natural or genetically-occurring anti-coagulant includes one or more of lupus anticoagulant or clotting factors VIII (8), IX (9), XI (11), or XII (12). Analyzing the two or more parameters may be performed using a model that relates the two or more parameters to known results for fibrinogen. Analyzing the two or more parameters may be performed using a model to distinguish the therapeutic or pharmaceutical anticoagulant from natural or genetically-occurring anticoagulant.

The one or more processing devices may be configured to obtain the clot curve for the test sample based on an assay performed on the test sample. The one or more parameters may be based on (i) one or more negative peaks determined using the clot curve, or (ii) widths of peaks determined using the clot curve. The one or more processing devices may be configured to determine, based on the one or more parameters, at least whether a therapeutic or pharmaceutical anti-coagulant is present in the test sample. The one or more processing devices may be configured to obtain a second derivative of the clot curve, and to determine the one or more parameters based on the second derivative of the clot curve. The one or more negative peaks may be in the second derivative of the clot curve.

The one or more processing devices may be configured to determine whether a therapeutic or pharmaceutical anticoagulant is present in the test sample by determining a number of the one or more negative peaks. The therapeutic or pharmaceutical anticoagulant may be present when there is a single negative peak. The one or more processing devices may be configured to obtain a second derivative of the clot curve, to identify positive and negative peaks in the second derivative of the clot curve, to identify widths of the positive and negative peaks, and to determine a ratio based on the widths. The one or more processing devices may be configured to determine whether a therapeutic or pharmaceutical anticoagulant is present in the test sample by comparing the ratio to a threshold. The therapeutic or pharmaceutical anticoagulant may be present when the ratio is below the threshold.

Another example system includes non-transitory machine-readable memory storing instructions that are executable and one or more processing devices to execute the instructions to perform operations that include: obtaining a clot curve for a test sample based on an assay performed on the test sample; obtaining one or more parameters based on the clot curve, where the one or more parameters are based on (i) one or more negative peaks determined using the clot curve or (ii) widths of peaks determined using the clot curve; determining, based on the one or more parameters, at least whether a therapeutic or pharmaceutical anticoagulant is present in the test sample; and outputting, on a user interface, information based on the determination. The example system may include one or more of the following features, either alone or in combination.

Obtaining one or more parameters may include obtaining a second derivative of the clot curve and determining the one or more parameters based on the second derivative of the clot curve. The one or more negative peaks may be in the second derivative of the clot curve. Determining whether a therapeutic or pharmaceutical anticoagulant is present in the test sample may include determining a number of the one or more negative peaks, where the therapeutic or pharmaceutical anticoagulant is present when there is a single negative peak.

Obtaining the one or more parameters may include obtaining a second derivative of the clot curve, identifying positive and negative peaks in the second derivative of the clot curve, identifying widths of the positive and negative peaks, and determining a ratio based on the widths. Determining whether a therapeutic or pharmaceutical anticoagulant is present in the test sample may include comparing the ratio to a threshold, where the therapeutic or pharmaceutical anticoagulant is present when the ratio is below the threshold. The therapeutic or pharmaceutical anticoagulant may include at least one of heparin or a direct oral anticoagulant (DOAC), where the DOAC includes at least one of apixaban, dabigatran, or rivaroxaban.

The information output on the user interface may include a recommendation to perform quantitative testing for the therapeutic or pharmaceutical anticoagulant.

An example method performed by one or more processing devices includes: analyzing a clot curve for a test sample that is based on an assay performed on the test sample in order to obtain two or more parameters associated with the clot curve, where the two or more parameters include two or more of: clot growth rate, clot formation duration, clot amplitude (which may include sigmoid magnitude range and/or clot curve range), clot baseline, clotting time, clot growth width, clot growth skew, or first, second, or third derivative features of the clot curve that include one or more of clot acceleration duration and/or shape, clot deceleration duration and/or shape, clot peaks width, clot peaks width ratio, clot peaks location, clot peaks number, clot velocity, clot peaks amplitude, clot peaks area under curve (AUC), shapes of clot peaks, peaks onset shape, peak offset shape, peak skewness, peak kurtosis, width at a peak baseline, width at a peak location other than peak baseline, peaks prominence, a parameter based on a maximum acceleration and zero crossing of the clot curve, a parameter based on the maximum acceleration and predefined threshold of the clot curve, or a parameter based on maximum and minimum acceleration of the clot curve; analyzing the two or more parameters to determine at least one of (i) whether a fibrinogen concentration in the test sample is below a threshold, or (ii) whether there is a therapeutic or pharmaceutical anticoagulant present in the test sample; and outputting, to a user interface, information based on the determination. The example method may include one or more of the following features, either alone or in combination.

An example method is described for obtaining information from a test sample. The method includes providing one or more processing devices adapted for: (i) analyzing a clot curve for the test sample that is based on an assay performed on the test sample in order to obtain two or more parameters associated with the clot curve, where the two or more parameters include two or more of: clot growth rate, clot formation duration, clot amplitude, clot baseline, clotting time, clot growth width, clot growth skew, or first and second derivative features of the clot curve comprising one or more of clot acceleration duration and/or shape, clot deceleration duration and/or shape, clot peaks width, clot peaks width ratio, clot peaks location, clot peaks number, clot velocity, clot peaks amplitude, clot peaks area under curve, shapes of clot peaks, peaks onset shape, peak offset shape, peak skewness, peak kurtosis, width at a peak baseline, width at a peak location other than peak baseline, peaks prominence, a parameter based on a maximum acceleration and zero crossing of the clot curve, a parameter based on the maximum acceleration and predefined threshold of the clot curve, or a parameter based on maximum and minimum acceleration of the clot curve; and (ii) analyzing the two or more parameters to determine at least one of (i) whether a fibrinogen concentration in the test sample is below a threshold, or (ii) whether there is a therapeutic or pharmaceutical anticoagulant present in the test sample. The method also includes outputting, to a user interface, information based on the determination.

In either method, the information may include one or more of: a recommendation to perform additional testing for fibrinogen or the therapeutic or pharmaceutical anticoagulant, or a concentration of fibrinogen in the test sample, or an identity of the therapeutic or pharmaceutical anticoagulant in the test sample. In either method, two or more parameters may be based on at least one of a first derivative of the clot curve or a second derivative of the clot curve. In either method, therapeutic or pharmaceutical anticoagulant may include at least one of heparin or a direct oral anticoagulant (DOAC), where the DOAC may include at least one of apixaban, dabigatran, or rivaroxaban. In either method, analyzing the two or more parameters to determine whether there is a therapeutic or pharmaceutical anticoagulant present in the test sample may include using the two or more parameters to distinguish the therapeutic or pharmaceutical anticoagulant from a natural or genetically-occurring anticoagulant, where the natural or genetically-occurring anticoagulant includes one or more of lupus anticoagulant or clotting factors VIII (8), IX (9), XI (11), or XII (12).

Any two or more of the features described in this specification, including in this summary section, can be combined to form implementations not specifically described herein.

The systems, processes, operations, components, and variations thereof described herein, or portions thereof, can be implemented using, or may be controlled by, a computer program product that includes instructions that are stored on one or more non-transitory machine-readable storage media, and that are executable on one or more processing devices. The systems, processes, operations, components, and variations thereof described herein, or portions thereof, can be implemented as an apparatus, method, or electronic systems that can include one or more processing devices and memory to store executable instructions to implement the various operations. The systems, processes, operations, components, and variations thereof described herein may be configured, for example, through design, construction, arrangement, placement, programming, operation, activation, deactivation, and/or control.

The details of one or more implementations are set forth in the accompanying drawings and the description below.

Other features, objects, and advantages will be apparent from the description and drawings, and from the claims.

DESCRIPTION OF THE DRAWINGS

Like reference numerals in different figures indicate like elements.

DETAILED DESCRIPTION

Described herein are example processes that may be implemented on a diagnostic test instrument or by one or more processing devices external to or remote from the diagnostic test instrument to provide clinicians with decision support. For example, as described below, the processes may be executed to analyze a routine test sample, such as a patient's blood or plasma, and to provide, based on the analysis, clinicians with recommendations about whether to perform specific follow-up testing for the patient. The follow-up testing may be to detect a fibrinogen concentration in the patient's blood or plasma and/or to detect the presence, type, and/or amount of therapeutic or pharmaceutical anticoagulant, such as heparin or direct oral anticoagulant (DOAC) (such as, but not limited to, apixaban, dabigatran, or rivaroxaban) in the patient's blood or plasma. In some implementations, the processes may provide the same information as the follow-up testing or estimates of that information without needing additional specialty assay testing.

Figure 1:
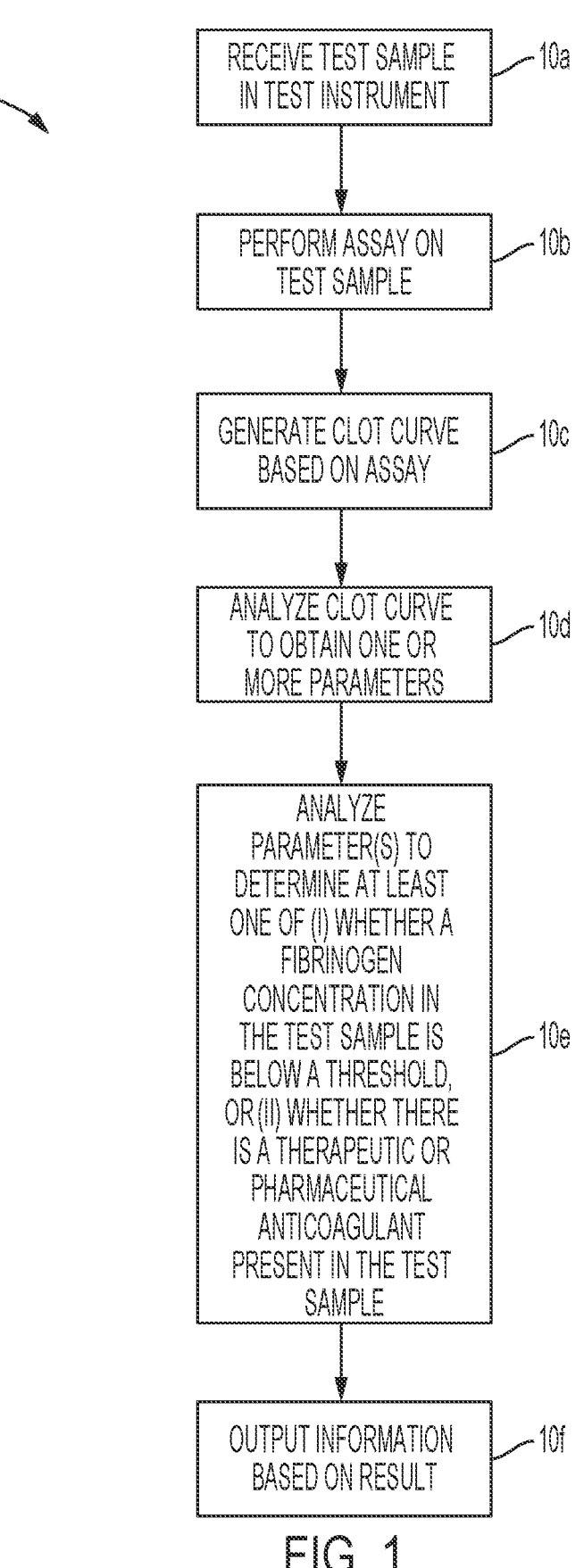
FIG. 1 is a flowchart showing operations included in an example process for providing clinical decision support.

FIG. 1 shows operations that may be performed on the diagnostic test instrument to implement an example process 10, such as that described above. The diagnostic test instrument may be a coagulation analyzer or include coagulation analyzer functionality. The diagnostic test instrument receives (10a) a test sample, such as a portion of the whole blood or plasma. The sample include one or more human blood or plasma. The sample include one or more human samples or animal samples. For example, the test sample may be loaded into a cartridge or cuvette that is then inserted into the diagnostic test instrument. In another example, the test sample may be pipetted directly into a sample receptacle contained in or to be used with the diagnostic test instrument.

The diagnostic test instrument performs (10b) one or more assays on the test sample to analyze coagulation of the test sample over time. Examples of assays that may be performed (10b) include, but are not limited to, screening assays such as the activated partial thromboplastin time (aPTT) test and the prothrombin time (PT) test. These assays are performed by an optical measurement system in the diagnostic test instrument that measures changes in transmittance, or absorbance, of a light beam through the test sample during coagulation of the test sample. The diagnostic test instrument generates (10c) a clot curve, also referred to as an absorption curve, based on data from one or both assays, which represents clotting of the test sample over time.

Figure 4:
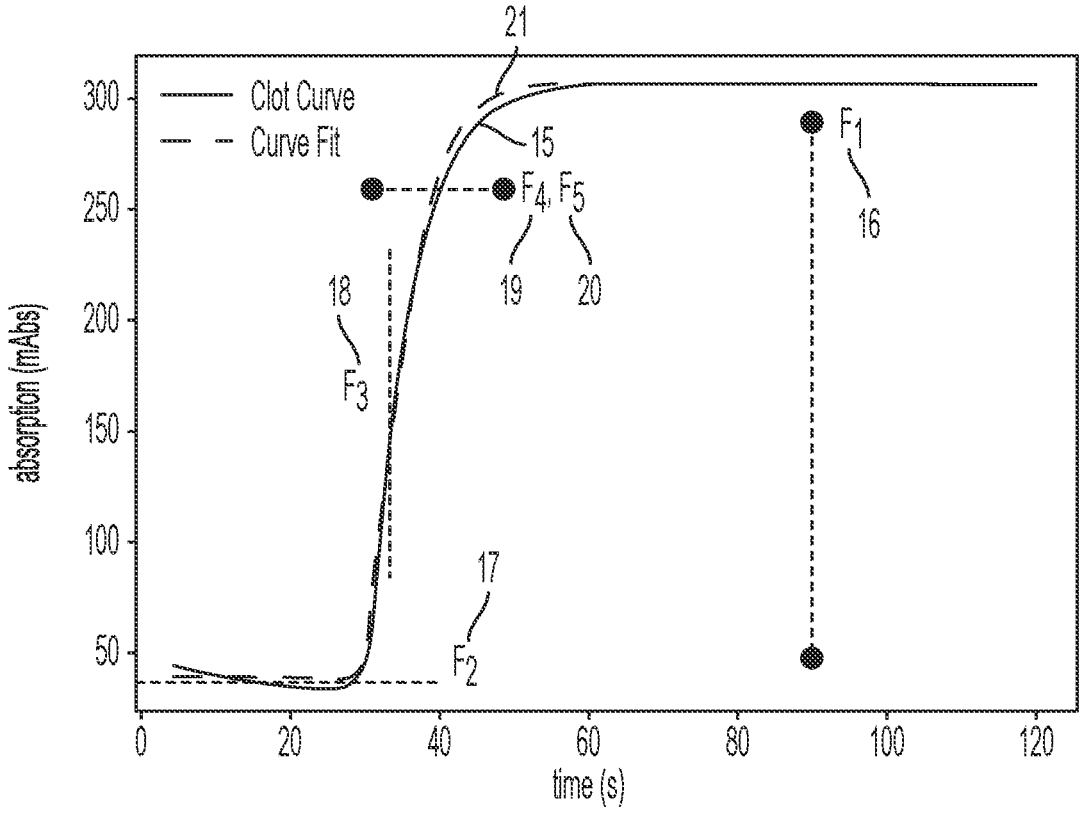
FIG. 4 is a graph showing an example clot curve and parameters thereof.

FIG. 4 shows an example of an aPTT clot curve 15. Clot curve 15 is a plot of the aPTT reaction which tracks clot formation as a function of time. Curve 15 can be fit with a parametrized sigmodial or logistic function. The sigmoidal function is characterized by a classic "S" or sigmoidal shape that fits the bottom and top plateaus of the curve, the EC50, and the slope factor (Hill's slope). The EC50 corresponds to S half maximal effective concentration, which is a measure of the concentration of a substance that induces a response halfway between a baseline and a maximum after a specified exposure time. The curve may be symmetrical around its inflection point.

Figures 2, 3:
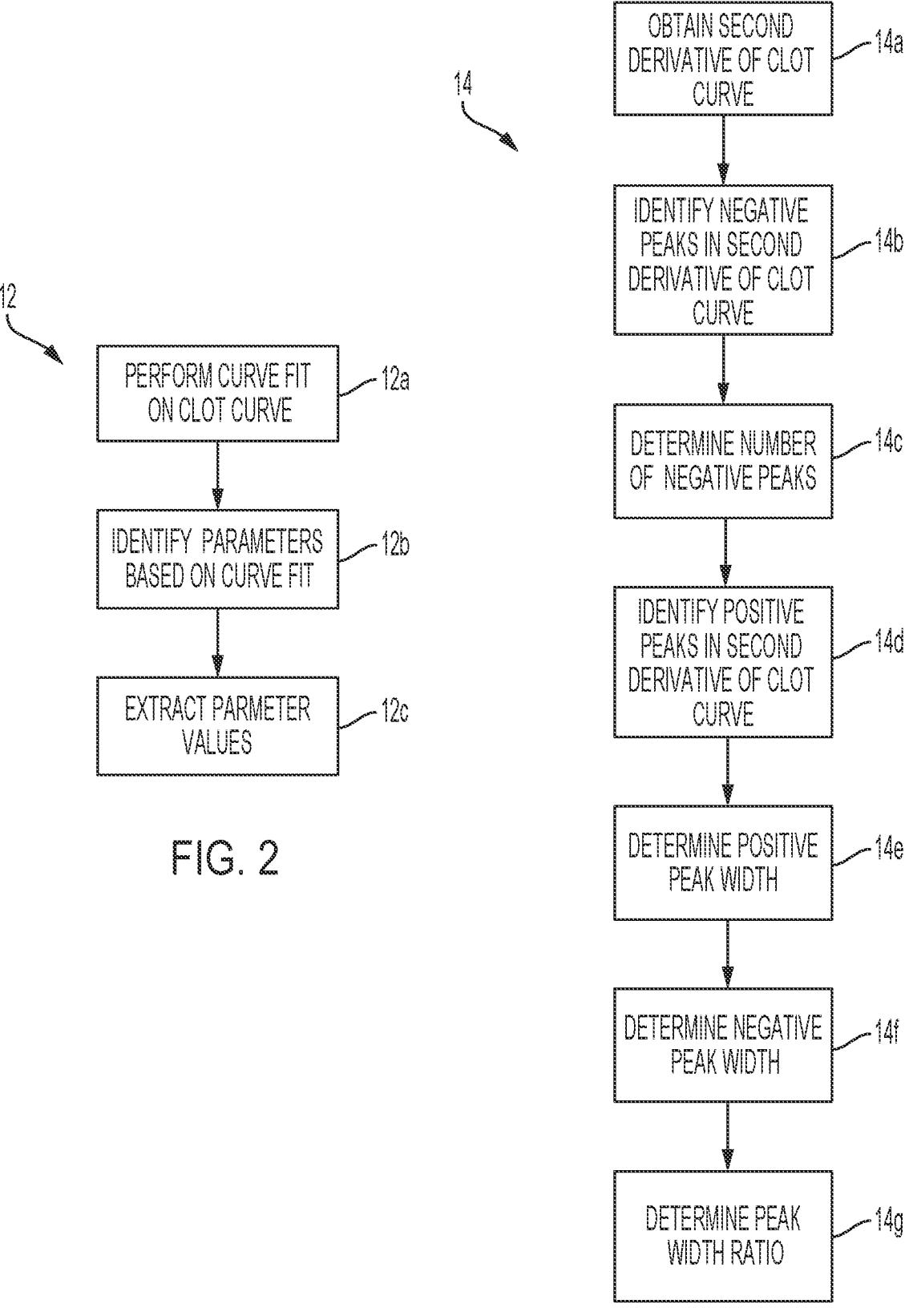
FIG. 2 is a flowchart showing operations included in an example process for obtaining parameters from a clot curve.
FIG. 3 is a flowchart showing operations included in an example process for obtaining parameters from a second derivative of a clot curve.

Parameters obtained based on the clot curve for a test sample are indicative of attributes of the clot or the clotting process that occurred for the test sample. FIGS. 2 and 3 show example processes 12 and 14, respectively, that may be performed on the diagnostic test instrument or on one or more processing devices that are external to or remote from the diagnostic test instrument for analyzing (10d) clot curves and derivatives thereof to obtain values for one or more of these parameters.

Process 12 of FIG. 2 may be executed to analyze (10d) clot curve 15. Clot curve 15 is analyzed (10d) to obtain parameters such as, but not limited to, clot amplitude 16 ($F_1$), clot baseline 17 ($F_2$), clotting time 18 ($F_3$), clot growth width 19 ($F_4$), and clot growth skew 20 ($F_5$). Process 12 of FIG. 2 includes performing (12a) a curve fit on clot curve 15. In the example of FIG. 4, a sigmoidal curve 21 is fit to clot curve 15. Symmetric sigmoidal curves, asymmetric sigmoidal curves with finite skew, and Frechet cumulative distribution curves are additional example of fitting functions that may be curve-fit to the clot curve.

The range of the sigmoidal curve and the shape of the first derivative peak may be correlated to fibrinogen levels. Sigmoidal curve 21 is analyzed to identify (12b) the foregoing parameters and, for each parameter, to extract (12c) a corresponding parameter value. For example, the value of clot baseline 17 is a low point on curve 21; the value of clot amplitude 16 is a difference between a low point and a high point of curve 21; the value of clotting time 18 is the curve feature related to the peak location of the second derivative of curve 21, the value of clot growth width 19 is the curve feature related to the width of the first derivative peak, and the value of the clot growth skew 20 is the curve feature that captures the shape and asymmetry in onset and the saturation of the curve. Different types of clot curves may be subjected the foregoing analyses to obtain parameters such as these. For example, a PT clot curve (not shown) may be similarly analyzed to obtain similar parameters, with some variations. For example, in a PT curve, clotting time is based on a peak of a first derivative of the clotting curve. Other parameters may be obtained, such as clotting acceleration and deceleration that are charactered by onset and saturation shapes of the curve. Additionally, features of curve sections having variable ranges, and of the whole curve, can be used to characterize the above features and to enhance inference thereof, and those features may also be determined based on the clotting curve.

Figure 5:
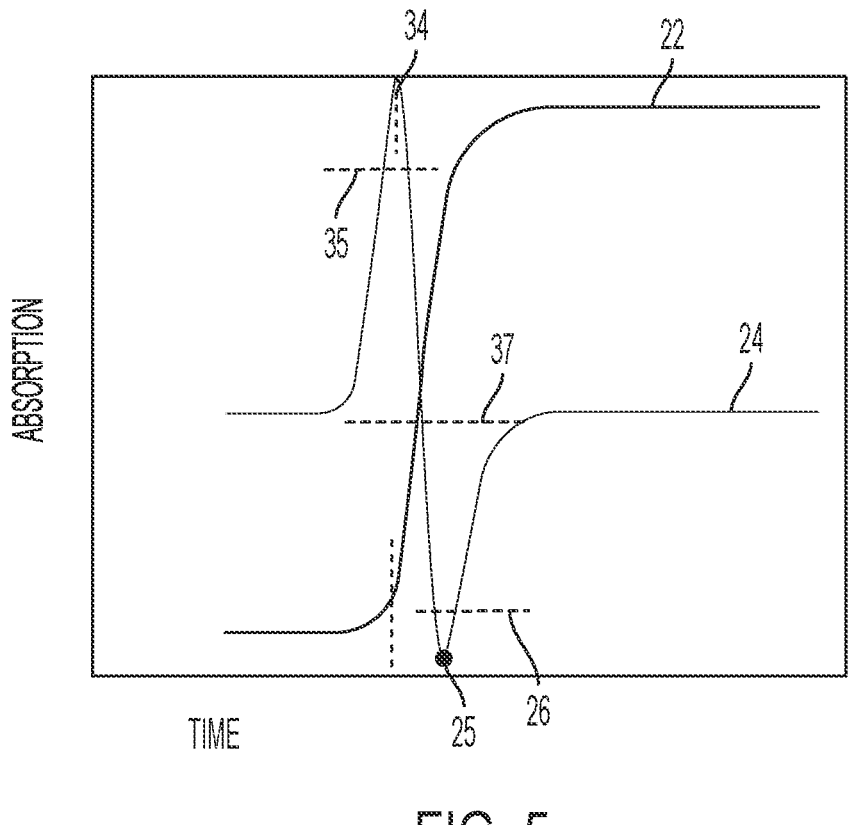
FIG. 5 is a graph showing an example clot curve and a second derivative thereof.

FIG. 5 shows an example of an aPTT clot curve 22 that is analyzed (10*d*, FIG. 1) based on its derivative. In this example, the derivative is a second derivative curve 24. An example of the analysis that may be performed by the diagnostic test instrument or on one or more processing devices that are external to or remote from the diagnostic test instrument is process 14 shown in FIG. 3. The operations of process 14 may be performed in the order shown or in an order that is different than that shown.

Process 14 includes obtaining (14) the second derivative curve 24 of clot curve 22. Analyses to obtain the parameters from second derivative curve 24 may be based on curve-fitting techniques. For example, one or more Gaussian functions or Lorentzian peak functions may be curve-fit to second derivative curve 24 and the one or more curve-fit functions may be analyzed to obtain one or more parameters.

The curve(s) fit to the second derivative curve are analyzed to identify (14*b*) one or more negative peaks in second derivative curve 24. An example of a negative peak is a location on the second derivative curve 24, such as negative peak 25, that is below a predefined threshold, such as predefined threshold 26, and that reaches a minimum value and then increases in value from the minimum value. The predefined threshold 26 may be determined experimentally and may be programmed into the diagnostic test instrument. Curve 24 includes a single negative peak 25; however, other example second derivative curves, such as second derivative curve 29 of FIG. 9, may include two negative peaks 29*a*, 29*b* (or more).

A curve having two negative peaks is called biphasic. This feature is common in curves having complicating factors associated with anticoagulant detection such as heparin. For example, complicating factors are common in samples with physiological conditions such as high lupus anticoagulant or low levels of coagulation factors that also prolong the aPTT result. The APTT result time is correlated to lupus anticoagulant levels. The width of the second peak of the two negative peaks is another parameter that may be used as part of the multi-parametric set of inputs used in the processes described herein.

In some cases a biphasic peak amplitude is not detectable in a second derivative curve alone, or a peak in the second derivative curve is reminiscent of an inflection point. In such cases, a third derivative of the clot curve may be obtained. The third derivative curve is analyzed to identify peaks in the third derivative curve. The peaks of the third derivative curves are analyzed to obtain parameters, such as peak shape, amplitude, width, and area-under-the-curve (AUC). In some cases, a combination of the second and third derivative curves are analyzed using empirically-determined amplitude multipliers to amplify bi-phasic peaks of each derivative curve. Properties of the amplified bi-phasic peaks are analyzed in a manner similar to analyses of peaks of first, second, and third derivative curves to obtain parameters, such as peak shape, amplitude, width, and AUC. The parameters obtained using third derivative curves may be used in the processes described herein.

Process 14 determines (14*c*), e.g., counts, the number of negative peaks(s) in the second derivative curve, such as curve 24 or 29, and uses that number as a parameter value in the processes described herein. In some implementations, value(s)/magnitudes of the negative peaks may be extracted from the second derivative curve and used as parameter value(s) in in the processes described herein. The negative curve peaks on the second derivative curve correspond to clot deceleration.

Process 14 also includes identifying (14*d*) a positive peak in the second derivative curve. The positive peak is identified by determining a location on second derivative curve 24, such as positive peak 34, that is above a predefined threshold, such as predefined threshold 35, and that reaches a maximum value and then decreases from the maximum value. The predefined threshold 35 may be determined experimentally and may be programmed into the diagnostic test instrument.

Figure 8:
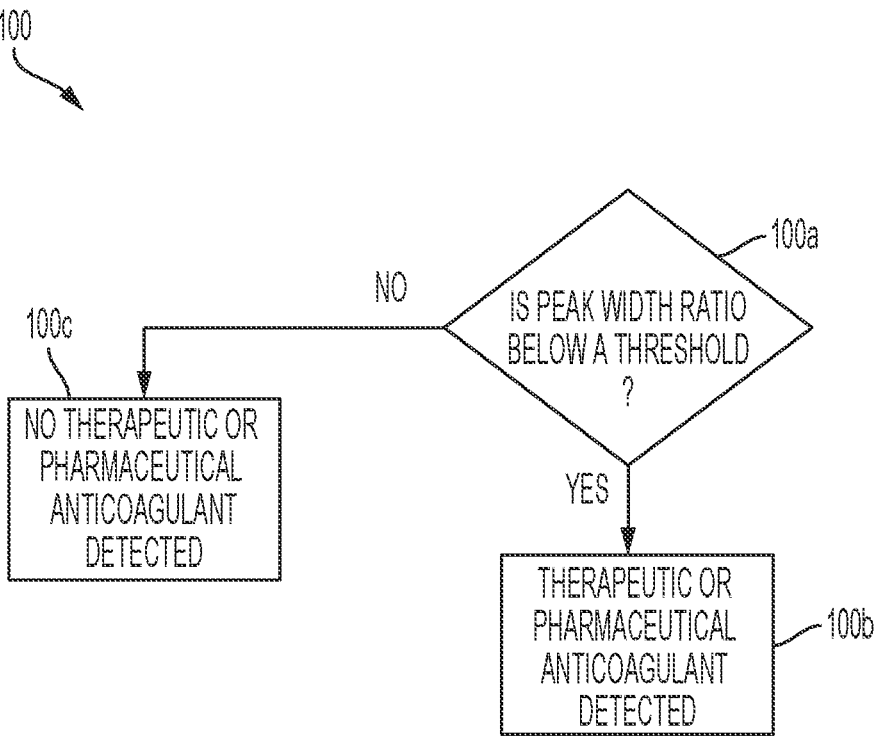
FIG. 8 is a flowchart showing operations included in another example process for identifying therapeutic or pharmaceutical anticoagulants in a test sample.
Figure 9:
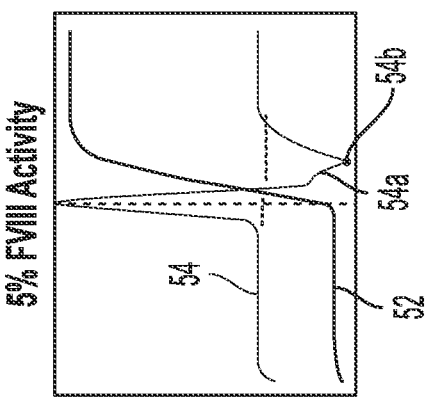
FIG. 9 includes graphs showing example clot curves and second derivatives thereof for heparin, lupus anticoagulant (LAC), and clotting factor VIII.
Figure 9:
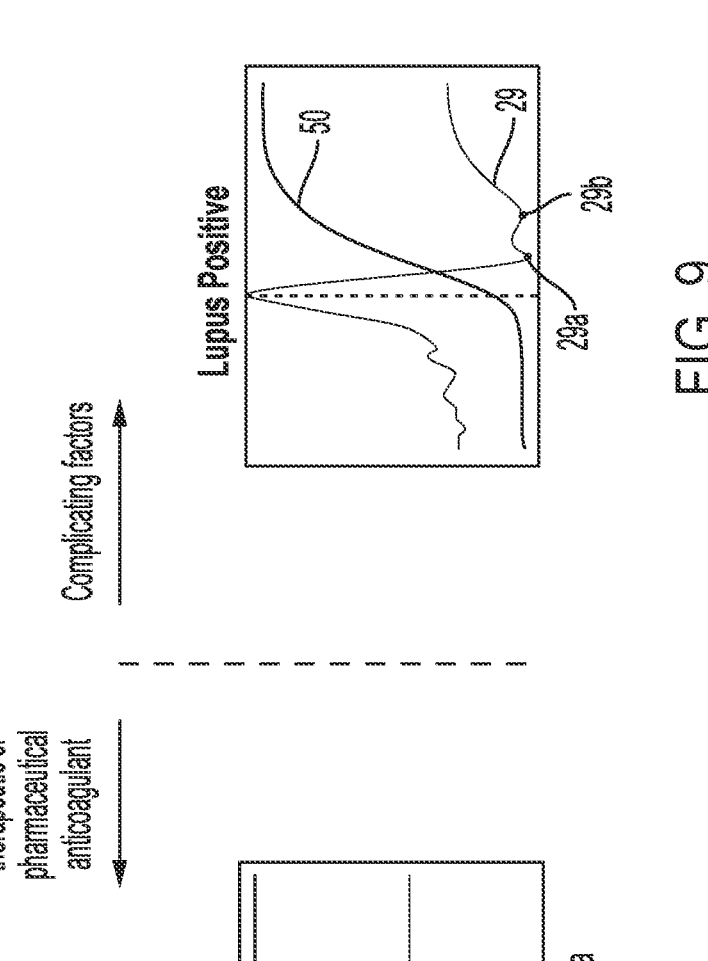

Process 14 also includes determining (14*e*) a width of the positive peak, such as positive peak 34, and determining (14*f*) a width of the negative peak such as negative peak 25 or a width of consecutive adjacent negative peaks as in FIG. 9 where negative peaks 29*a*, 29*b* are biphasic. The locations where the widths are measured in each peak may be at about the same predefined location for each of the peaks. These locations where the peak widths are measured may be determined experimentally and may be programmed into the diagnostic test instrument. For example, the location where the peak widths are measured may be at or near a peak second derivative baseline 37 (FIG. 5), a point half-way up or down each peak, or at some other location along the longitudinal dimension/height of each peak. The peak widths are combined to determine (14*g*) a peak width ratio. The peak width ratio is determined by the diagnostic test instrument or one or more processing devices external to or remote from the instrument. The ratio may be the ratio of the width of the negative peak to the positive peak (e.g., negative peak width divided by (/) positive peak width), vice versa, or some variation thereof. In the example described with respect to FIG. 8, the peak width ratio is defined as negative peak width/positive peak width.

Parameters in addition to, those described previously may be determined based on the first and second derivatives of the clot curves 24. Examples of such parameters include, but are not limited to the second order derivative clot peaks locations, peaks amplitude, width, area under the curve (AUC), and shapes. Clot peak locations may be defined as the locations of the positive peak and/or the negative peak at the second derivative baseline 37. Clot peak amplitude may be defined as the value/magnitude of the positive peak 34 on the second derivative curve. Other parameters that can be obtained from the second derivative curve include clot acceleration, which is based on the positive peak in the second derivative curve and its onset and offset shapes, and clot deceleration, which is based on one or more negative peaks in the second derivative curve and their onset and offset shapes. Additionally, features of the first and/or second derivative curves sections of variable range, and of the whole curves can be used to characterize the above features and to enhance inferences.

Figure 12:
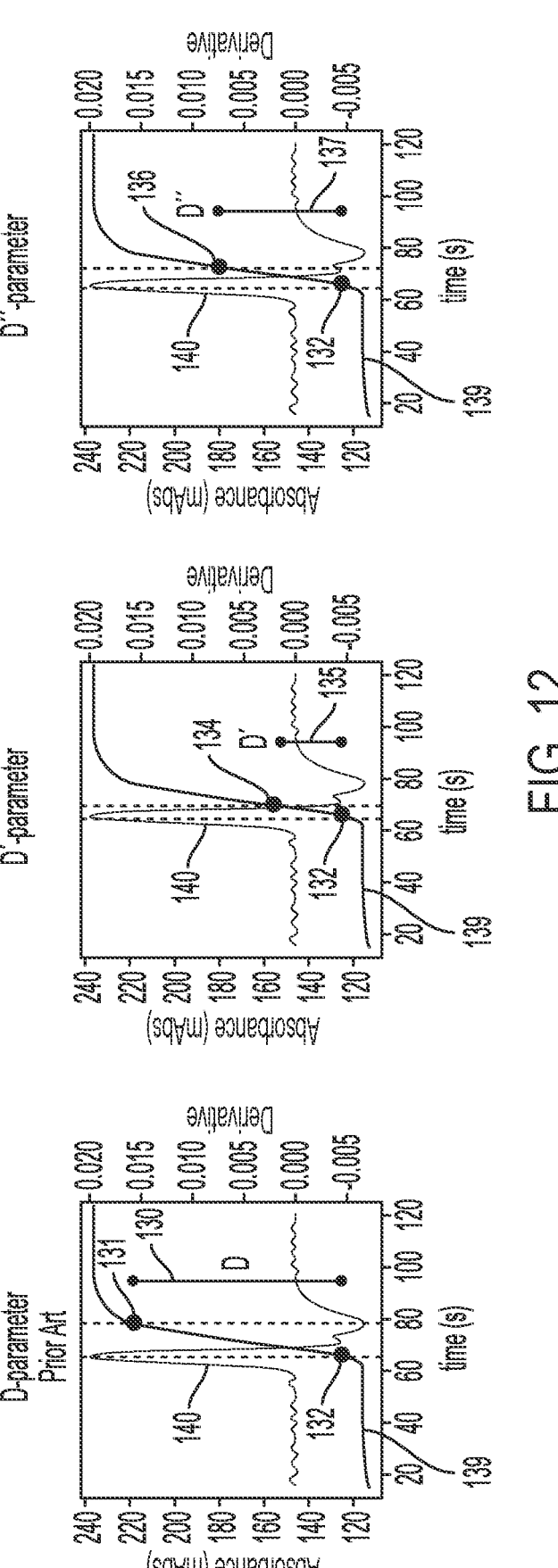
FIG. 12 includes graphs showing example clot curves and second derivatives thereof showing modifications to the standard D-parameter.

Other parameters may be determined based on the clot curve of FIG. 12, which contains example clot curve 139 and a second derivative 140 thereof. As shown in FIG. 12, a process for estimating fibrinogen concentration from a PT clot curve uses a single parameter, called the D-parameter 130, which is defined as the difference in absorbance between the time points of the maximum 132 and minimum 131 acceleration of the clot curve. When the reaction curve does not have a simple sigmoidal shape, either because it has additional inflection points, or peaks that have ill-defined maxima, the D-parameter can be error prone. Alternatives to the D-parameter, D' 135 and D" 137, can be defined that accommodate clot curves that are not purely sigmoidal, such as by defining the two time-points of the D' parameter as the maximum acceleration 132 and acceleration zero-crossing 134, or by defining the two time-points of the D''' parameter as the maximum acceleration 132 and a specific clot curve normalized threshold 136, such as 50% (or 40%, 30%, 20%, or the like) of its absorbance travel. These modifications D' and D" can have an improved correlation (relative to the standard D-parameter) with the fibrinogen concentration in samples that are anticoagulated, factor deficient, or contain inhibitors.

To summarize, examples of the parameters that may be obtained (10d) include, but are not limited to: clot growth rate, clot formation duration, clot amplitude (which may include sigmoid magnitude range and/or clot curve range), clot baseline, clotting time, clot growth width, clot growth skew, and first and second derivative features of the clot curve that include one or more of clot acceleration duration and/or shape, clot deceleration duration and/or shape, clot peaks width, clot peaks width ratio, clot peaks location, clot peaks number, clot velocity, clot peaks amplitude, clot peaks area under curve (AUC), shapes of clot peaks, peaks onset shape, peak offset shape, peak skewness, peak kurtosis, width at a peak baseline, width at a peak location other than peak baseline, peaks prominence, D, D', or D".

Referring back to FIG. 1, process 10 includes analyzing (10e) one or more of the obtained (10d) parameters to determine at least one of (i) whether a fibrinogen concentration in the test sample is below a threshold, or (ii) whether there is one or more therapeutic or pharmaceutical anticoagulant present in the test sample and, in some implementations, the identity(ies) and/or concentrations thereof. Both analyses may be performed for the same test sample or only one analysis may be performed for the test sample. In some cases, clinician or programmatic input may determine whether one or both analyses is to be performed. In some cases, the diagnostic test instrument or other processing device(s) may be preprogrammed to perform only one or both of the analyses. Any thresholds used to perform the analyses may be determined experimentally and may be programmed into the diagnostic test instrument or other processing device(s).

Figure 6:
FIG. 6 is a flowchart showing operations included in an example process for identifying a fibrinogen concentration and/or therapeutic or pharmaceutical anticoagulants in a test sample.
Figure 6:
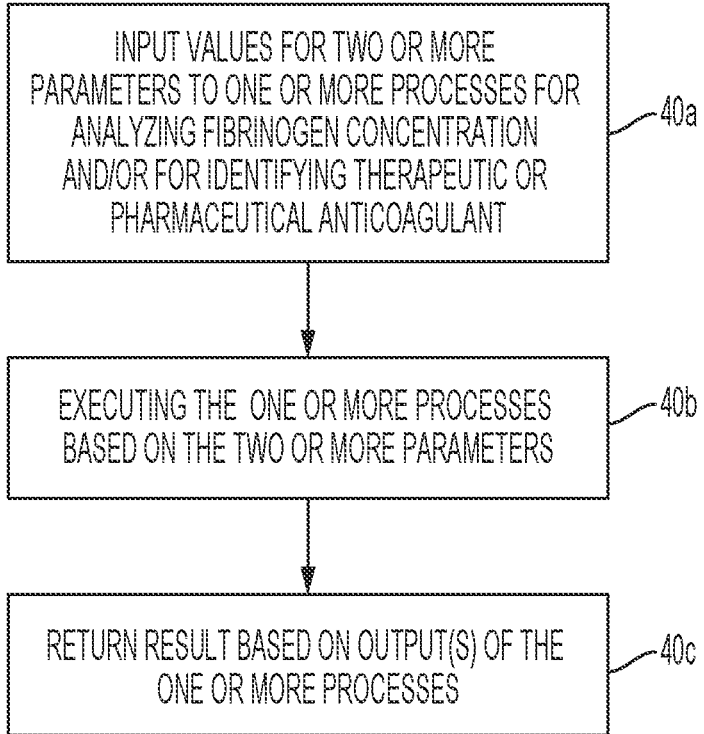

Various techniques may be used to implement the analysis (10e) of FIG. 1. For example FIG. 6 shows example operations (40) that may be executed to perform the analysis. In some implementations, the operations may be performed by the diagnostic test instrument and/or by one or more processing devices that are external to, or remote from, the diagnostic test instrument. As shown in FIG. 6, performing the analysis includes inputting (40a) values for two or more of the obtained (10d) parameters to one or more processes for analyzing fibrinogen concentration in the test sample and/or for identifying a therapeutic or pharmaceutical anticoagulant (e.g., DOACs such as apixaban, dabigatran, and/or rivaroxaban) in the test sample. The values for the two or more parameters may be input from other routines running on the diagnostic test instrument or other one or more other devices. For example, the two or more parameters may be input from processes 12 (FIG. 2) and/or 14 (FIG. 3).

Operations for analyzing fibrinogen (40a) concentration in the test sample may be implemented using various techniques. For example, parameters that affect coagulation and that are useful in identifying fibrinogen concentration may be identified experimentally in a laboratory, using machine learning techniques, or using processes that do not use machine learning techniques. In example implementations that use machine learning techniques, a machine learning model relates known parameter inputs to known fibrinogen concentrations. The model may be trained on a computing system external to the diagnostic test instrument using supervised learning techniques. The model's type can be a machine learning regressor or classifier that includes, but is not limited to, multiple regression, decision trees and random forests, neural networks, support vector machines (SVMs), or ensemble methods, such as gradient boosting. Supervised machine learning techniques, such as neural net, gradient boosting, and SVM, can be employed to build a model by examining examples and attempting to find a model that minimizes the loss; this process is called empirical risk minimization. If the model's predictions are accurate, the loss approaches zero; otherwise, the loss is greater, which results in higher penalty during training. The goal of training a model is to find a set of weights and biases that have low loss, on average, across all examples to reach process robustness and generalization.

The model for analyzing the fibrinogen concentration may analyze, but is not limited to analyzing, permutations of two or more of the following parameters associated with a clot curve or derivative thereof including parameters associated with clot formation, such as clot growth rate, clot formation duration, clot amplitude (which may include sigmoid magnitude range and/or clot curve range), clot baseline, clotting time, clot growth width, clot growth skew, or first and second derivative features of the clot curve such as one or more of clot acceleration duration and/or shape, clot deceleration duration and/or shape, clot peaks width, clot peaks width ratio, clot peaks location, clot peaks number, clot velocity, clot peaks amplitude, clot peaks area under curve, shapes of clot peaks, peaks onset shape, peak offset shape, peak skewness, peak kurtosis, width at a peak baseline, width at a peak location other than peak baseline, peaks prominence, D, D', or D". The model may be stored in computer memory on the diagnostic test instrument or in memory that external to, or remote from, the diagnostic test instrument. The model may be used on the diagnostic test instrument and/or by one or more processing devices that are external to, or remote from, the diagnostic test instrument. The model may be static, meaning that it does not change following installation. Among alternative examples, the operations for analyzing fibrinogen concentration in the test sample based on two or more of the foregoing parameters may be implemented using computer programs, algorithms, and/or other types of executable functions either alone or in combination with the model described above.

In the case of fibrinogen, the accuracy of estimating fibrinogen concentration based on two or more parameters associated with a clot curve may be better than processes that use a single parameter. It is known that the curve delta of a clot curve for a test sample is proportional to the fibrinogen concentration in the test sample, but additional factors may cause this correlation to be reduced for an optical measurement system. Polymerized fibrinogen or fibrin produces optical scattering that can be measured, so an optical signal produced by the optical measurement system may be proportional to the amount of fibrin strands produced. In addition to the total amount of fibrin strands produced, the optical signal also may be proportional to the size of each strand, where larger strands produce larger scattering. It is known that different plasma samples may produce different fibrin strand sizes based on the clotting proteins and inhibitors in each sample. A sample that contains a fixed amount of fibrinogen can produce different curve deltas depending on whether the sample coagulates to form many small strands or fewer large strands. As a result, curve parameters such as clotting time and clotting velocity may be correlated to the curve delta, and not just sample fibrinogen concentration.

In addition to clot formation kinetics, optical measurement systems have a nonlinear relationship between concentration of a scatterer and measured absorbance. In a system where light can be multiply scattered, or where the mean free path of the light is less than a sample holder path length, there is a sublinear attenuation with fibrinogen concentration. This results in a smaller delta absorbance with greater scattering. This greater scattering can be caused by either a very high fibrinogen concentration or a high scattering background caused by lipemia. As a result, another parameter of the clot waveform, the baseline absorbance (clot baseline 17 ($F_2$)), is correlated to the curve delta and can be factored into the operations described herein for analyzing fibrinogen concentration.

By using two or more parameters to analyze fibrinogen concentration as described herein, the analysis may improve the precision of the derived fibrinogen estimate for PT and provide a new derived fibrinogen estimate for APTT.

Operations (40a) for determining the presence and/or identity of one or more therapeutic or pharmaceutical anticoagulant, and/or concentrations thereof in the test sample may be implemented using various techniques. For example, parameters that affect coagulation and that are useful in identifying therapeutic or pharmaceutical anticoagulants and/or concentrations thereof may be identified experimentally in a laboratory or using machine learning techniques.

In this regard, therapeutic or pharmaceutical anticoagulants may inhibit the initiation of clot formation, but once clot formation begins, clot formation may happen at a similar rate as in normal blood or plasma. In contrast, for blood or plasma that is coagulation factor depleted or that has insufficient phospholipids, clot formation may be similarly inhibited, but once it begins, clot formation may proceed more slowly because it is still deficient in a key reactant. This is evident by manual inspection of a clot curve where the result time may be dependent on when clot formation starts, but clot formation may be completed much sooner for the same result time in the presence of therapeutic or pharmaceutical anticoagulants than for complicating factors such as lupus anticoagulant or clotting factors VIII (8), IX (9), XI (11), or XII (12).

The clotting rate is dependent on the polymerization mechanisms in the test sample, where test samples that are missing a key reactant produce fewer, but larger fibrinogen polymers. Test samples that contain therapeutic or pharmaceutical anticoagulants produce many, but smaller, fibrinogen polymers. Because polymer nucleation has different kinetics than polymer growth, these test samples have different clot curves. The clot formation rate and acceleration (first and second derivative) are not simple unimodal functions in the presence of complicating factors, such as such as lupus anticoagulant or clotting factors VIII (8), IX (9), XI (11), or XII (12). The clot formation rate and acceleration typically are unimodal functions for prolonged coagulation caused by therapeutic or pharmaceutical anticoagulants, where prolonged coagulation is with respect to a sample that does not include therapeutic or pharmaceutical anticoagulants. The clot formation rate and acceleration in the presence of complicating factors can impact clot deceleration (as can be seen, for example in the second derivative negative peaks 29a, 29b of FIG. 9) and is repeatable among replicates, so the negative peaks in of the second derivative curve acts as a unique signature of the kinetics of that particular sample.

Input test values may be analyzed using machine learning techniques or other processes that do not use machine learning to distinguish therapeutic or pharmaceutical anticoagulant from natural or genetically-occurring anticoagulant such as, but not limited to, lupus anticoagulant (LAC) or clotting factors VIII (8), IX (9), XI (11), or XII (12). In the machine learning example, the parameters that affect coagulation and that are useful in identifying therapeutic or pharmaceutical anticoagulants and/or concentrations thereof may be part of a machine learning model configured to distinguish, based on input test values, therapeutic or pharmaceutical anticoagulant from natural or genetically-occurring anticoagulant. In the machine learning example, the model receives values of the parameters and distinguishes, based on the input test values, therapeutic or pharmaceutical anticoagulant from natural or genetically-occurring anticoagulant. The model is configured to analyze the input test values to determine whether clot prolongation is due to therapeutic or pharmaceutical anticoagulants. The sample is analyzed based on two or more parameters such as, but not limited to, those listed above and repeated here: clot growth rate, clot formation duration, clot amplitude (which may include sigmoid magnitude range and/or clot curve range), clot baseline, clotting time, clot growth width, clot growth skew, or first and second derivative features of the clot curve such as one or more of clot acceleration duration and/or shape, clot deceleration duration and/or shape, clot peaks width, clot peaks width ratio, clot peaks location, clot peaks number, clot velocity, clot peaks amplitude, clot peaks area under curve, shapes of clot peaks, peaks onset shape, peak offset shape, peak skewness, peak kurtosis, width at a peak baseline, width at a peak location other than peak baseline, peaks prominence, D, D', or D". Examples of such a model that may be used are described above include, but are not limited to, a neural network, gradient boosting, and an SVM. The model may be stored in computer memory on the diagnostic test instrument or memory that is external to, or remote from, the diagnostic test instrument. In some implementations, the model may be static, meaning that it may not change following installation. In some implementations, the model may be updated.

The processes for identifying a therapeutic or pharmaceutical anticoagulant and/or concentrations thereof in the test sample based on two or more of the foregoing parameters may be implemented using computer programs, algorithms, and/or other type of executable functions stored on the diagnostic test instrument or external to or remove from the diagnostic test instrument, either alone or in combination with the machine learning techniques described herein.

In some implementations, a combined model, decision tree, XGBoost (Xtreme Gradient Boosting), SVM, neural network, computer program, algorithm, and/or other type of executable function may be stored on the diagnostic test instrument and/or on one or more processing devices external to or remote from the diagnostic test instrument both to analyze any two or more of the above parameters to determine fibrinogen concentration and to determine a presence of therapeutic or pharmaceutical anticoagulant (and/or a concentration thereof) in the test sample. Alternatively, separate such models, multiple regression, decision trees, gradient boosting, SVM's, neural networks, XGBoost, computer programs, algorithms, and/or other type of executable functions may be stored on the test instrument or external to or remote from the test instrument—one model for fibrinogen and one model for therapeutic or pharmaceutical anticoagulant. In some implementations, multiple regression may be useful approach for maximum interpretability particularly for fibrinogen.

Referring back to FIG. 6, the diagnostic test instrument or a remote processing system executes (40b) one or more of the processes—e.g., models, multiple regression, decision trees, gradient boosting, neural networks, SVM's, computer programs, algorithms, and/or other type of executable functions—using values of the parameters received/obtained in operation (40a) in order to identify a fibrinogen concentration in the test sample and/or the presence of therapeutic or pharmaceutical anticoagulant in the test sample and, potentially, an identity and/or concentration of the therapeutic or pharmaceutical anticoagulant in the test sample. In the case of fibrinogen, the result of the execution may be a concentration of fibrinogen in the test sample. In the case of therapeutic or pharmaceutical anticoagulant, the result of the execution may be one or more of: (i) an indication that a therapeutic or pharmaceutical anticoagulant is present in the test sample, or (ii) an identification of the type of therapeutic or pharmaceutical anticoagulant present in the test sample. For example, for an APTT curve, the processes can provide a clinical decision support indication of likelihood and ranking of each of these components. A quantitative indication of the amount of anticoagulant may also be provided. The quantitative indication itself may be provided for fibrinogen (improved derived fibrinogen, and new for APTT). For anticoagulants and complicating factors, the processes may guide a user toward a likely quantitative specialty assay(s).

The result of process 40 of FIG. 6 is returned (40c) to process 10 of FIG. 1. Process 10 outputs (10f) information on a user interface (UI) on the diagnostic test instrument or other display device that is based on the received result. The information may include one or both of a concentration of fibrinogen in the test sample or an identity, presence, and/or a concentration of the therapeutic or pharmaceutical anticoagulant in the test sample. The information may include a recommendation to perform additional quantitative testing for fibrinogen and/or the therapeutic or pharmaceutical anticoagulant for the patient. For example, the concentration of fibrinogen may be compared to an experimentally-predefined threshold stored in memory. If that concentration of fibrinogen is below that threshold, then a recommendation for additional fibrinogen testing may be output (10f) to identify or to confirm the fibrinogen concentration. In another example, any identification of the therapeutic or pharmaceutical anticoagulant in the test sample may precipitate output (10f) of a recommendation for additional testing to be performed to identify or to confirm types and/or quantities of the therapeutic or pharmaceutical anticoagulant.

As noted above, different techniques may be used to implement the analysis (10e) of FIG. 1. Other example of such techniques, which are described with respect to FIGS. 7 and 8 below, may be part of, or used alone or in combination with, the technique described above with respect to FIG. 6.

Figure 7:
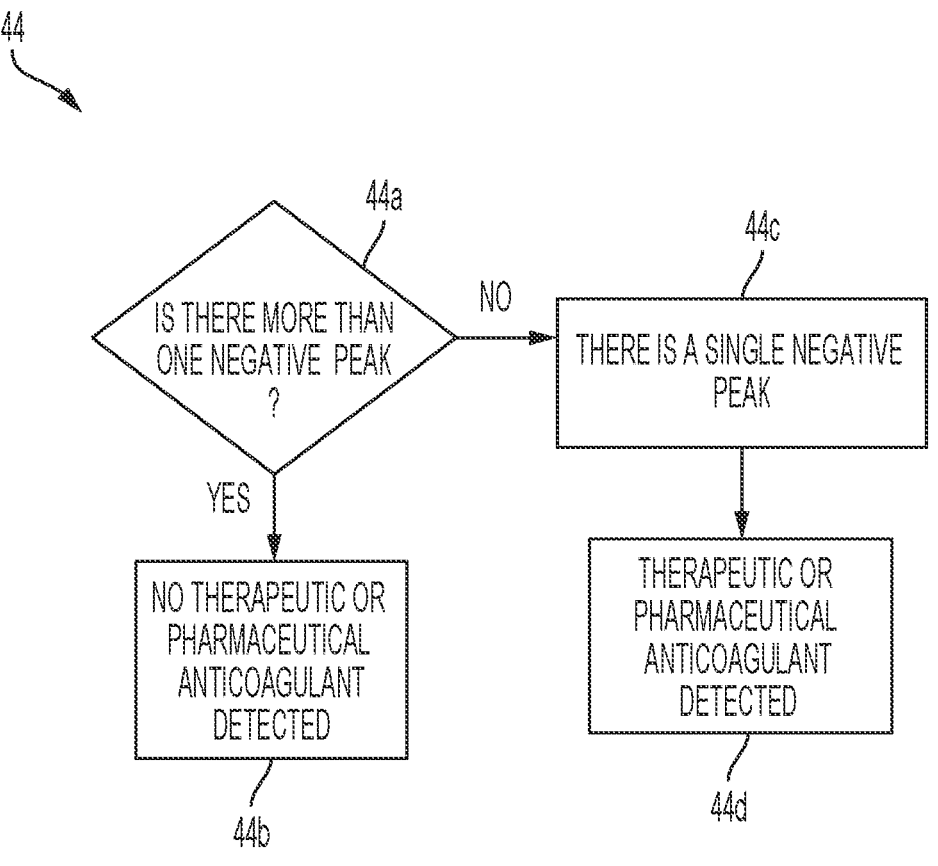
FIG. 7 is a flowchart showing operations included in an example process for identifying therapeutic or pharmaceutical anticoagulants in a test sample.

FIG. 7 shows example operations included in a process 44 that may be performed on the diagnostic test instrument and/or on one or more processing devices external to or remote from the diagnostic test instrument to identify therapeutic or pharmaceutical anticoagulant in the test sample using one or more second derivative curve minima, where the second derivative is of the clotting curve. The presence of multiple second derivative minima is correlated with aPTT-dependent coagulation factor activities and lupus anticoagulant concentrations which may be present naturally in the human body, but not therapeutic or pharmaceutical anticoagulant concentrations. As shown in FIG. 7, process 44 determines (44a) whether there is more than one negative peak in the second derivative curve of a clot curve for a test sample. If there is more than one negative peak, then no therapeutic or pharmaceutical anticoagulant is detected (44b) in the test sample. If there is a single negative peak (44c), then a therapeutic or pharmaceutical anticoagulant is detected (44d) in the test sample. Notably, if there is a single negative peak, process 44 relies on a single parameter to make its decision.

FIG. 9 shows an example of a clot curve 46 having prolonged clotting time, where the prolonged clotting time is relative to a sample that does not include low molecular weight (LMW) heparin, and corresponding second derivative curve 47 in the presence of LMW heparin; FIG. 9 also shows an example of a clot curve 50 having prolonged clotting time, where the prolonged clotting time is relative to a sample that does not include lupus anticoagulant, and its corresponding second derivative curve 29 in the presence of lupus anticoagulant; and FIG. 9 also shows an example of a clot curve 52 having prolonged clotting time, where the prolonged clotting time is relative to a sample that has a normal factor VIII (8) level, and corresponding second derivative curve 54 in the presence of an abnormal factor VIII (8) level. Second derivative curve 47 has a single negative peak 47a, which is commensurate with the presence of heparin or, more generally, a therapeutic or pharmaceutical anticoagulant. Second derivative curve 29 has a two negative peaks 29a and 29b, which is commensurate with a complicating factor, which is lupus anticoagulant in this example, whereas a single negative peak indicates that the complicating factor is not present. Second derivative curve 54 has two negative peaks 54a and 54b, which is commensurate with a complicating factor, which is the presence of an abnormal factor VIII (8) level in this example, whereas a single negative peak indicates that the complicating factor is not present.

Figure 10:
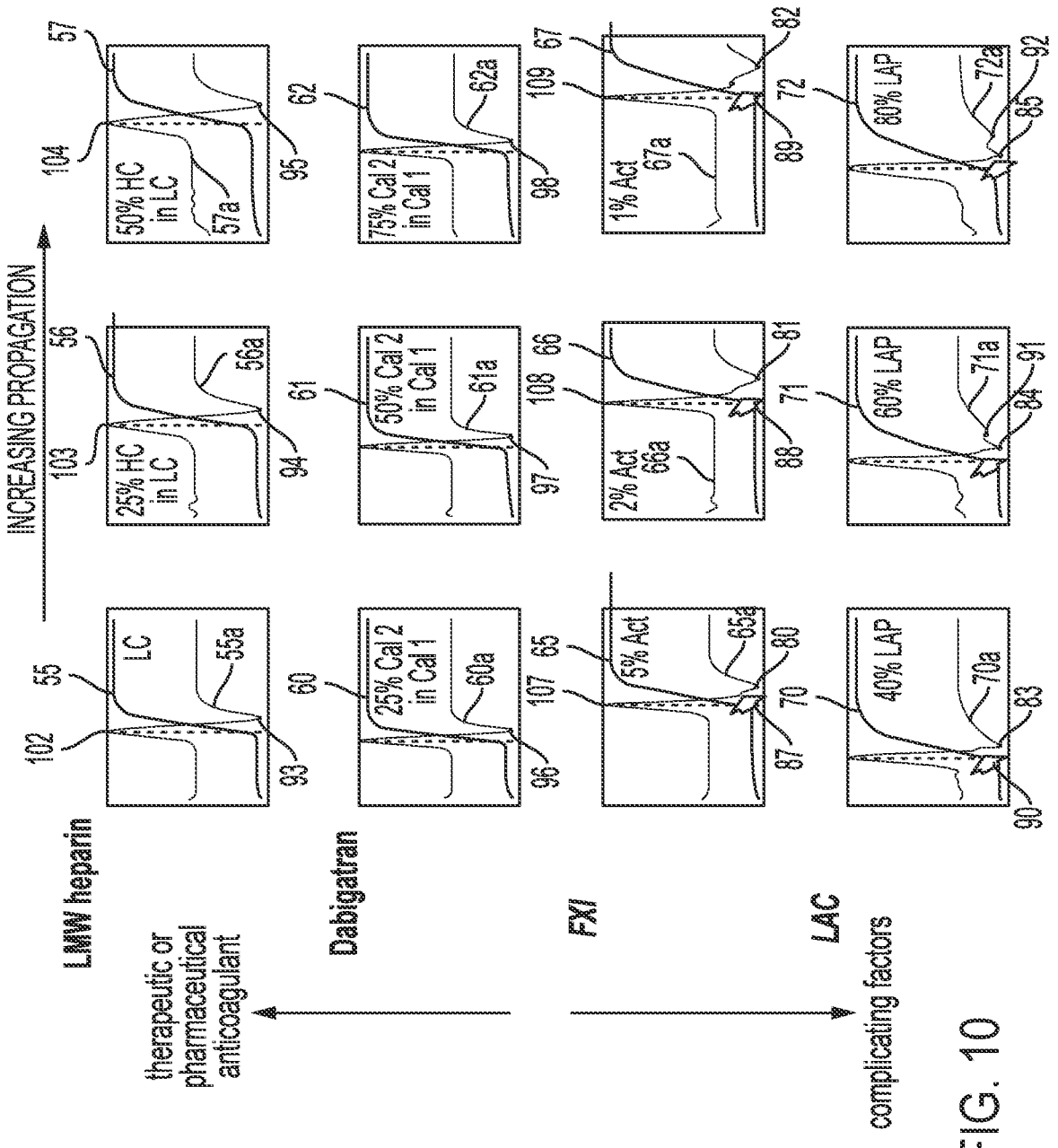
FIG. 10 includes graphs showing examples of a clot curves and second derivatives thereof for heparin, dabigatran, clotting factor XI, and lupus anticoagulant.

In other examples, FIG. 10 shows examples of clot curves 55, 56, and 57 having prolonged clotting times and corresponding second derivative curves 55a, 56a, and 57a in the presence of LMW heparin for increasing clot propagation from left to right. FIG. 10 shows examples of clot curves 60, 61, and 62 having prolonged clotting times and corresponding second derivative curves 60a, 61a, and 62a in the presence of dabigatran for increasing clot propagation going from left to right. FIG. 10 shows examples of clot curves 65, 66, and 67 having prolonged clotting times and corresponding second derivative curves 65a, 66a, and 67a for a sample having abnormal clotting factor XI (FXI) levels for increasing clot propagation going from left to right. FIG. 10 shows examples of clot curves 70, 71, and 72 having prolonged clotting times and corresponding second derivative curves 70a, 71a, and 72a in the presence of lupus anticoagulant for increasing clot propagation going from left to right.

As shown in FIG. 10 for lupus anticoagulant (LAC) and clotting factor XI (FXI), the negative peaks are biphasic, that is there are primary negative peaks 80 to 85 and respective secondary negative peaks 87 to 92. As shown in FIGS. 10, for therapeutic or pharmaceutical anticoagulants—LMW heparin and dabigatran in this example—the negative peaks 93 to 98 are unimodal.

Curves 55, 56, and 57 thus may be used to detect the presence of LMW heparin using the techniques described herein. Curves 60, 61, and 62 may be used to detect the presence of dabigatran using the techniques described herein. Curves 107, 108, and 109 may be used to detect the presence of clotting factor XI (FXI) using the techniques described herein. Curves 70, 71, and 72 may be used to detect the presence of lupus anticoagulant (LAC) using the techniques described herein.

The result of process 44 of FIG. 7 is returned to process 10 of FIG. 1. Process 10 outputs (10*f*) information on a UI on the diagnostic test instrument or other display device that is based on the result from process 40. The information may include a recommendation to perform additional quantitative testing for the therapeutic or pharmaceutical anticoagulant.

FIG. 8 shows example operations included in another process 100 that may be performed on the diagnostic test instrument and/or on one or more processing devices external to or remote from the diagnostic test instrument to identify therapeutic or pharmaceutical anticoagulant in the test sample. As shown in FIG. 8, process 100 determines (100*a*) whether the peak width ratio of a second derivate clot curve is below a predefined threshold. The predefined threshold may be determined experimentally or using machine learning techniques and may be programmed into the diagnostic test instrument or other external or remote devices that perform process 100. The predefined threshold may be set experimentally so as to distinguish therapeutic or pharmaceutical anticoagulants from complicating factors such as those described herein. An example of the predetermined threshold for one feature 1.6; however, that threshold may vary based on test instrument, anticoagulants, test protocols, and the like, e.g., the threshold may be 1.7, 1.8, 1.9, 2.0, and so forth. If the peak width ratio is below the predefined threshold then a therapeutic or pharmaceutical anticoagulant is detected (100*b*) in the test sample. If the peak width ratio is above the predefined threshold, then no therapeutic or pharmaceutical anticoagulant is detected (100*c*) in the test sample.

Referring to FIG. 10, for example, for second derivative curves 55*a* to 57*a* for a test sample containing LMW heparin, the width of each positive peak 102 to 104 and the widths of respective negative peaks 93 to 95 (for example, determined at the second derivative curve baseline—see 37, FIG. 5) are relatively close in value. By contrast, for second derivative curves 65*a* to 67*a* for a test sample containing abnormal clotting factor XI, the combined widths of the biphasic negative peaks 80, 87; 81, 88; and 82, 89, (for example, determined at the second derivative curve baseline) are considerably larger than the widths of respective positive peaks 107, 108, and 109. As a result, the peak width ratio (e.g., negative peak width/positive peak width) is greater for the clotting factor XI case than for the LMW heparin case. The peak width ratio for the clotting factor XI case therefore will exceed the predefined threshold described above, whereas the peak width ratio for the LMW heparin case will not. Dabigatran produces a similar result to heparin and lupus anticoagulant produces a similar result to factor XI. In this way, therapeutic or pharmaceutical anticoagulant can be distinguished from complicating factors.

The result of process 100 of FIG. 8 is returned to process 10 of FIG. 1 (e.g., whether a therapeutic or pharmaceutical anticoagulant is detected). Process 10 outputs (10*f*) information on a UI on the diagnostic test instrument or other display device that is based on the result. The information may include a recommendation to perform additional testing for the therapeutic or pharmaceutical anticoagulant.

Figure 11:
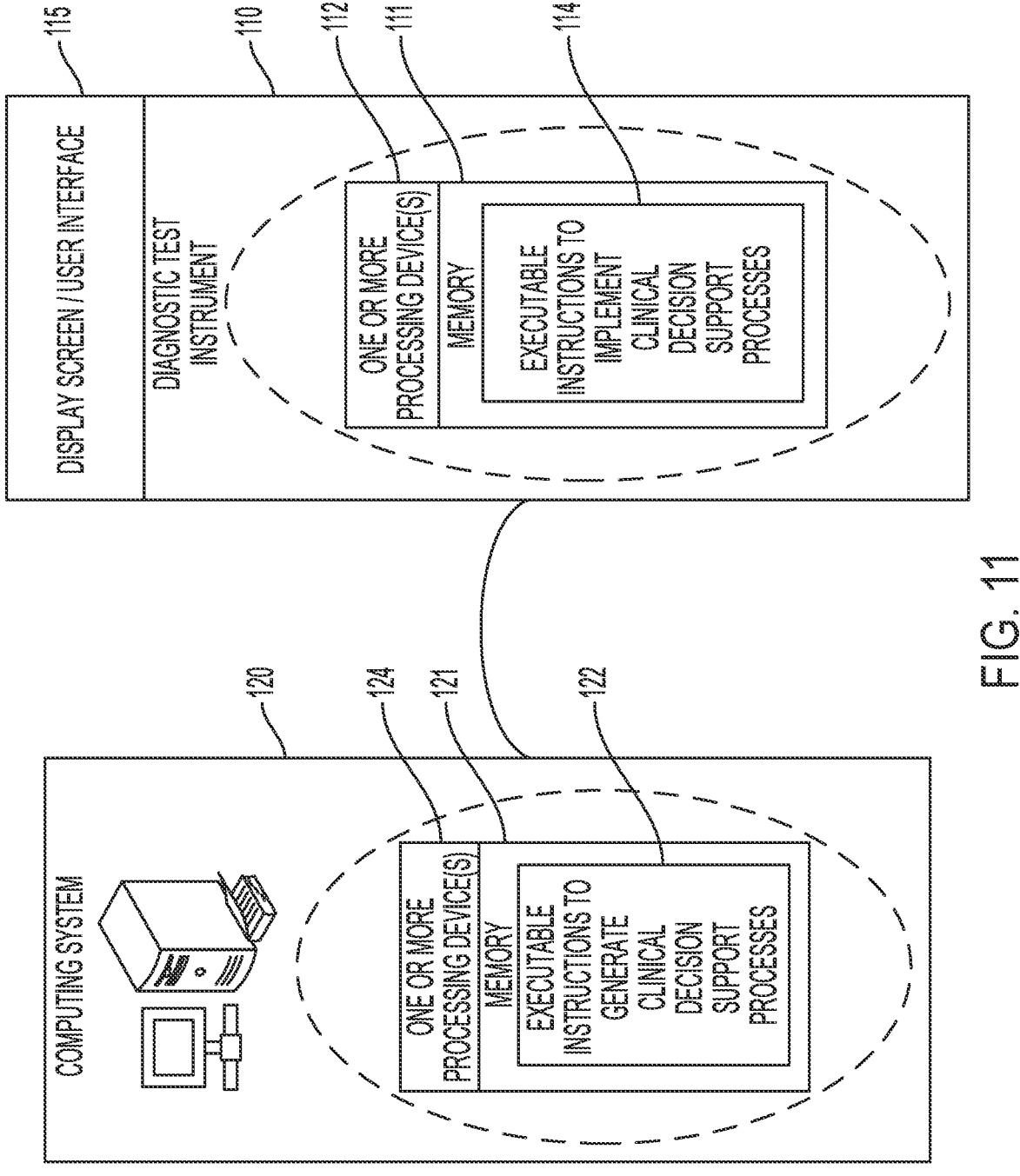
FIG. 11 is a block diagram of an example diagnostic test instrument and computing system.

FIG. 11 shows an example of diagnostic test instrument 110 on which the processes described herein may be implemented. Diagnostic test instrument 110 includes machine-readable memory 111 storing executable instructions 114 to implement the clinical decision support processes described herein. One or more processing devices 112, such as those described herein may execute the instructions to implement the model, multiple regression, decision trees, gradient boosting, SVM's, neural networks, computer programs, algorithms, and/or other type of executable functions to perform all or part of the processes of FIGS. 1, 2, 3, 6, 7, and 8 and any other programmatic functions described herein. A display screen or UI 115 may be configured to receive inputs and to generate outputs of the type described herein. In some implementations, the UI may be a graphical UI or a textual UI. The UI could be a software on the ACL TOP device or other similar device, or software in a remote computer that receives the data of the device, which is dedicated to analysis for clinical decision support applications. Alternatively, the processes and their outputs could be integrated into the device primary software as an overlay option to the device results, or offered as add-on software functionalities.

FIG. 11 also shows an example of a computing system 120 that includes machine-readable memory 121 storing executable instructions 122 to generate executable instructions for the model, multiple regression, decision trees, gradient boosting, SVM's, neural networks, computer programs, algorithms, and/or other type of executable functions. Instructions 122 may be executed by one or more processing devices 124. In some implementations, the diagnostic test instrument may communicate information, such as clinical decision support results to the computing system, although that is not a requirement.

The processes described herein may be implemented using any computing systems or any other appropriate computing device. Systems and processes can be implemented, at least in part, using one or more computer program products, e.g., one or more computer program tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the processes can be performed by one or more programmable processors executing one or more computer programs to perform the functions described herein. All or part of the processes can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random-access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Elements of different implementations described herein may be combined to form other implementations not specifically set forth above. Elements may be left out of the structures described herein without adversely affecting their operation. Operations in flowcharts may be performed, where appropriate, in different orders than those shown. Various separate elements may be combined into one or more individual elements to perform the functions described herein.

What is claimed is:

1. A system comprising:
non-transitory machine-readable memory storing instructions that are executable; and
one or more processing devices to execute the instructions to perform operations comprising:
performing an analysis based on a clot curve for a test sample, the clot curve being based on an assay performed on the test sample, the analysis being performed in order to obtain one or more parameters associated with the clot curve, the one or more parameters being selected from a D'-parameter, a D"-parameter, or both the D'-parameter and the D"-parameter, wherein the D' parameter is a difference in absorbance between time points of maximum acceleration and acceleration zero-crossing of the clot curve, and the D"-parameter is a difference in absorbance between time points of maximum acceleration and a threshold of an absorbance travel of the clot curve;
analyzing the one or more parameters to determine at least one of (i) whether a fibrinogen concentration in the test sample is below a threshold, or (ii) whether there is a therapeutic or pharmaceutical anticoagulant present in the test sample; and
outputting, on a user interface, information based on the determination.

2. The system of claim 1, wherein the information comprises a recommendation to perform additional testing for fibrinogen or the therapeutic or pharmaceutical anticoagulant.

3. The system of claim 1, wherein the information comprises a concentration of fibrinogen in the test sample or an identity of the therapeutic or pharmaceutical anticoagulant in the test sample.

4. The system of claim 1, wherein the one or more parameters is the D'-parameter only.

5. The system of claim 1, wherein the therapeutic or pharmaceutical anticoagulant comprises at least one of heparin or a direct oral anticoagulant (DOAC), the DOAC comprising at least one of apixaban, dabigatran, or rivaroxaban.

6. The system of claim 5, wherein analyzing the one or more parameters to determine whether there is a therapeutic or pharmaceutical anticoagulant present in the test sample comprises using the one or more parameters to distinguish the therapeutic or pharmaceutical anticoagulant from a natural or genetically-occurring anticoagulant, the natural or genetically-occurring anticoagulant comprising one or more of lupus anticoagulant or clotting factors VIII (8), IX (9), XI (11), or XII (12).

7. The system of claim 1, wherein analyzing the one or more parameters is performed using a model that relates the one or more parameters to known results for fibrinogen.

8. The system of claim 1, wherein analyzing the one or more parameters is performed using a model to distinguish the therapeutic or pharmaceutical anticoagulant from natural or genetically-occurring anticoagulant.

9. A system comprising:
non-transitory machine-readable memory storing instructions that are executable; and
one or more processing devices to execute the instructions to perform operations comprising:
obtaining a clot curve for a test sample based on an assay performed on the test sample;
obtaining one or more parameters based on the clot curve by performing operations comprising;
obtaining a second derivative of the clot curve;
identifying a positive peak and a negative peak in the second derivative of the clot curve;
identifying a first width of the negative peak and a second width of the positive peak; and
determining a ratio of the first width to the second width;
determining, based at least on the ratio whether a therapeutic or pharmaceutical anticoagulant is present in the test sample; and
outputting, on a user interface, information based on the determination.

10. The system of claim 9, wherein determining whether a therapeutic or pharmaceutical anticoagulant is present in the test sample comprises determining that the therapeutic or pharmaceutical anticoagulant being is present when the negative peak is the only negative peak in the second derivative of the clot curve.

11. The system of claim 9, wherein determining whether a therapeutic or pharmaceutical anticoagulant is present in the test sample comprises comparing the ratio to a threshold, the therapeutic or pharmaceutical anticoagulant being present when the ratio is below the threshold.

12. The system of claim 9, wherein the therapeutic or pharmaceutical anticoagulant comprises at least one of heparin or a direct oral anticoagulant (DOAC), the DOAC comprising at least one of apixaban, dabigatran, or rivaroxaban.

13. The system of claim 9, wherein the information comprises a recommendation to perform quantitative testing for the therapeutic or pharmaceutical anticoagulant.

14. The system of claim 9, wherein the ratio comprises the first width divided by the second width.

15. The system of claim 9, wherein the ratio comprises the second width divided by the first width.

16. A method performed by one or more processing devices, the method comprising:
performing an analysis based on a clot curve for a test sample, the clot curve being based on an assay performed on the test sample, the analysis being performed in order to obtain one or more parameters associated with the clot curve, the one or more parameters being selected from a D'-parameter, a D"-parameter, or both the D'-parameter and the D"-parameter, wherein the D' parameter is a difference in absorbance between time points of maximum acceleration and acceleration zero-crossing of the clot curve, and the D"-parameter is a difference in absorbance between time points of maximum acceleration and a threshold of an absorbance travel of the clot curve;

analyzing the one or more parameters to determine at least one of (i) whether a fibrinogen concentration in the test sample is below a threshold, or (ii) whether there is a therapeutic or pharmaceutical anticoagulant present in the test sample; and outputting, to a user interface, information based on the determination.

17. The method of claim 16, wherein the information comprises one or more of:

a recommendation to perform additional testing for fibrinogen or the therapeutic or pharmaceutical anticoagulant; or a concentration of fibrinogen in the test sample or an identity of the therapeutic or pharmaceutical anticoagulant in the test sample.

18. The method of claim 16, wherein the one or more parameters is the D'-parameter only.

19. The method of claim 16, wherein the therapeutic or pharmaceutical anticoagulant comprises at least one of heparin or a direct oral anticoagulant (DOAC), the DOAC comprising at least one of apixaban, dabigatran, or rivaroxaban; and wherein analyzing the one or more parameters to determine whether there is a therapeutic or pharmaceutical anticoagulant present in the test sample comprises using the one or more parameters to distinguish the therapeutic or pharmaceutical anticoagulant from a natural or genetically-occurring anticoagulant, the natural or genetically-occurring anticoagulant comprising one or more of lupus anticoagulant or clotting factors VIII (8), IX (9), XI (11), or XII (12).

* * * * *